(12) United States Patent
Broome

(10) Patent No.: US 6,391,050 B1
(45) Date of Patent: May 21, 2002

(54) SELF-EXPANDING STENT DELIVERY SYSTEM

(75) Inventor: Thomas E. Broome, Shakopee, MN (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/515,180

(22) Filed: Feb. 29, 2000

(51) Int. Cl.[7] .................................................. A61F 2/06
(52) U.S. Cl. ..................................................... 623/1.11
(58) Field of Search .......................... 623/1.11–1.2, 12; 606/194–197, 108, 198, 192, 191; 604/96.01, 103.05; 600/433–435, 585

(56) References Cited

U.S. PATENT DOCUMENTS

| | | | |
|---|---|---|---|
| 5,443,907 A | | 8/1995 | Slaikeu et al. |
| 5,534,007 A | * | 7/1996 | St. Germain et al. ....... 606/194 |
| 5,690,644 A | * | 11/1997 | Yurek et al. ................. 606/108 |
| 5,772,669 A | * | 6/1998 | Vrbra .......................... 606/108 |
| 5,782,855 A | * | 7/1998 | Lau et al. .................... 606/194 |
| 5,807,520 A | | 9/1998 | Wang et al. |
| 5,891,154 A | | 4/1999 | Loeffler |
| 5,968,052 A | | 10/1999 | Sullivan, III et al. |
| 5,968,069 A | * | 10/1999 | Dusbabek et al. .......... 606/194 |
| 6,017,577 A | | 1/2000 | Hostettler et al. |
| 6,042,588 A | * | 3/2000 | Mu nsinger et al. ........ 606/108 |
| 6,120,522 A | * | 9/2000 | Vrba et al. .................. 606/190 |

FOREIGN PATENT DOCUMENTS

| | | |
|---|---|---|
| WO | 97/26936 | 7/1997 |
| WO | 97/48343 | 12/1997 |
| WO | 98/20812 | 5/1998 |
| WO | 98/23241 | 6/1998 |
| WO | 98/52496 | 11/1998 |

* cited by examiner

Primary Examiner—Michael J. Milano
Assistant Examiner—(Jackie) Tan-Uyen T. Ho
(74) Attorney, Agent, or Firm—Vidas, Arrett & Steinkraus

(57) ABSTRACT

A stent delivery catheter is provided with a retractable sheath operated by a pull wire in mechanical communication with the sheath. The pullwire is carried in a pullwire lumen and exits from the pullwire lumen through an axial slit in the distal end of the pullwire lumen. The length of the axial slit is at least equal to the length of the sheath to be retracted to expose the stent for deployment.

24 Claims, 5 Drawing Sheets

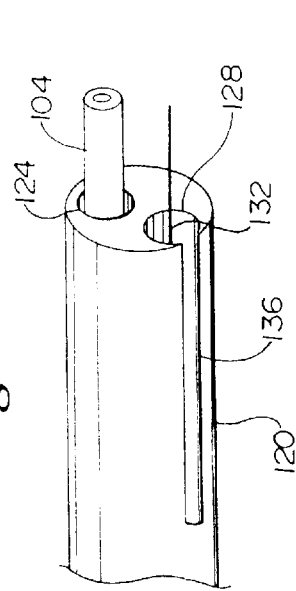
*Fig. 2a*
*Fig. 2b*
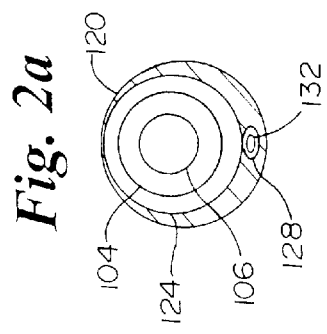
*Fig. 3*
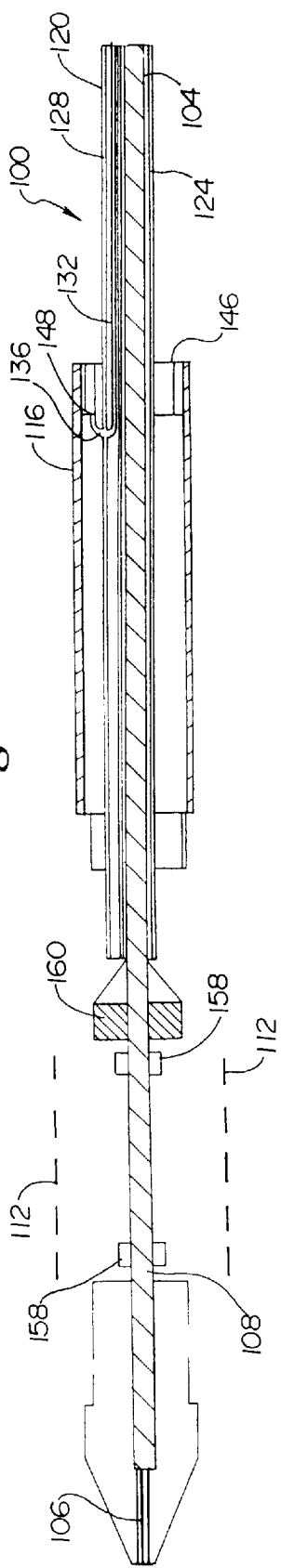

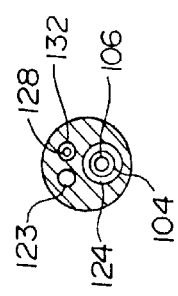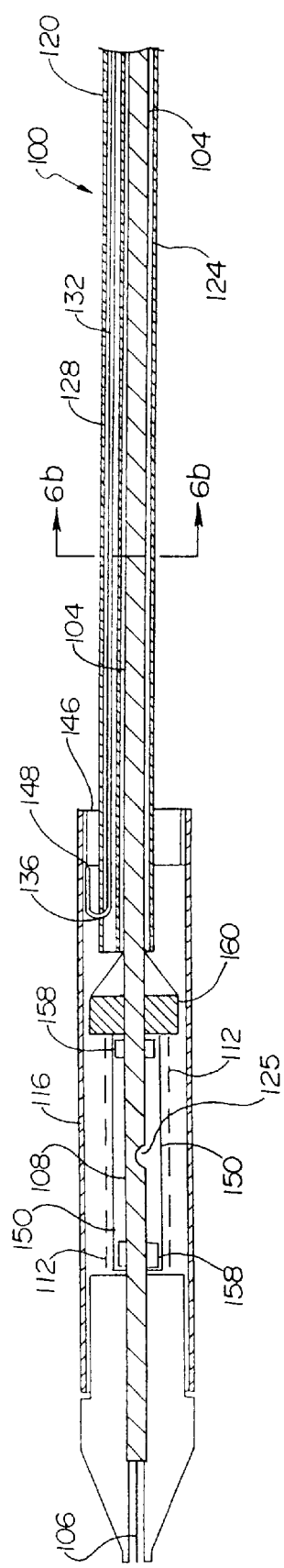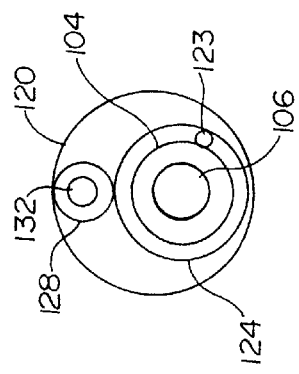

SELF-EXPANDING STENT DELIVERY SYSTEM

BACKGROUND OF THE INVENTION

In typical PTCA procedures, a guiding catheter is percutaneously introduced into the cardiovascular system of a patient and advanced through the aorta until the distal end is in the ostium of the desired coronary artery. Using fluoroscopy, a guide wire is then advanced through the guiding catheter and across the site to be treated in the coronary artery. An over the wire (OTW) balloon catheter is advanced over the guide wire to the treatment site. The balloon is then expanded to reopen the artery. The OTW catheter may have a guide wire lumen which is as long as the catheter or it may be a rapid exchange catheter wherein the guide wire lumen is substantially shorter than the catheter. Alternatively, a fixed wire balloon may be used. This device features a guide wire which is affixed to the catheter and cannot be removed.

To help prevent arterial closure, repair dissection, or prevent restenosis, a physician can implant an intravascular prosthesis, or a stent, for maintaining vascular patency inside the artery at the lesion. The stent may either be a self-expanding stent or a balloon expandable stent. For the latter type, the stent is often delivered on a balloon and the balloon is used to expand the stent. The self-expanding stents may be made of shape memory materials such as Nitinol or constructed of regular metals but of a design which exhibits self expansion characteristics.

An exemplary stent delivery catheter is disclosed in commonly assigned U.S. Pat. No. 5,772,669 to Vrba. The Vrba catheter has a retractable distal sheath concentrically arranged around a stent and a pull back means operatively connected to the distal sheath. The catheter is constructed and arranged such that at least the proximal end portion of the retractable sheath is received inside an outer body portion of the catheter on retraction of the sheath. In retracting the sheath, a length of sheath in excess of the length of the stent is moved. In the process of retracting the sheath, there is typically a frictional interaction between the sheath and the vessel wall.

In a catheter having a full length sheath, the frictional interaction between the sheath and the vessel wall may become more significant, possible resulting in motion of the distal end of the catheter relative to the vessel wall which, in turn, may result in decreased accuracy in the deployment of a stent.

For the purpose of this disclosure, all US patents and patent applications and all other publications referenced herein are incorporated herein by reference in their entirety.

BRIEF SUMMARY OF THE INVENTION

It is desirable to provide a medical device deployment catheter having improved deployment accuracy. Such a device may be provided in the form of a catheter in which the length of those portions of the catheter which are in contact with a vessel and which move on deployment of the medical device are of reduced length.

To that end, the present invention in one embodiment is directed to a stent delivery catheter comprising a guidewire lumen for receiving a guidewire therein. A stent is disposed about the distal end of the guidewire lumen and is covered by a retractable sheath disposed about the distal end of the guidewire lumen. The retractable sheath may be retracted by pulling on a pullwire in mechanical communication with the retractable sheath. The pullwire is disposed within a pullwire lumen. A slit of a predetermined length is provided in the pullwire lumen to allow for egress of the pullwire. The distal end of the pullwire extends from the pullwire lumen at the slit.

In another embodiment, the invention is directed to a medical device delivery catheter which comprises an inner tube with a medical device bearing region at the distal end. A retractable sheath is disposed about the medical device bearing region of the inner tube. The retractable sheath is controlled by a pullwire which is in mechanical communication with the retractable sheath. The pullwire extends proximally therefrom and is carried in a pullwire lumen. A slit is provided in the pullwire lumen for egress of the pullwire therefrom. The length of the slit exceeds the length of the medical device to be delivered. Desirably, the length of the stent will be approximately equal to the length of that portion of the retractable sheath which extends from the proximal end of medical device bearing region of the catheter and terminates at the distal end of sheath.

BRIEF DESCRIPTION OF THE SEVERAL VIEWS OF THE DRAWING(S)

FIG. 2a shows a transverse cross-sectional view of the catheter of FIG. 1 taken along line 2a—2a.

FIG. 2b shows a perspective view of the dual lumen with an axial slit in the pullwire lumen.

FIG. 3 shows the catheter of FIG. 1 with the sheath fully retracted.

FIG. 6a shows a cross-sectional view of the distal end of an inventive catheter configured for use as a fixed wire catheter.

FIG. 6b is a transverse cross-sectional view of the catheter of FIG. 6a taken along line 6b—6b.

FIG. 6c is a transverse cross-sectional view of a catheter similar to that shown FIG. 6a with an inflation lumen external to the guidewire lumen.

DETAILED DESCRIPTION OF THE INVENTION

While this invention may be embodied in many different forms, there are described in detail herein specific preferred embodiments of the invention. This description is an exemplification of the principles of the invention and is not intended to limit the invention to the particular embodiments illustrated.

The inventive catheters are intended for use in delivering deployable medical devices to a desired location in the body. Desirably, the medical devices are of the radially expandable tubular type. Particularly suitable radially expandable tubular medical devices for use with the inventive catheter include stents, stent-grafts, grafts, vena cava filters and other intraluminal and interluminal prostheses. The devices may be self-expanding or mechanically expandable via balloons or other expansion devices. For the sake of brevity, the term 'stent' as used henceforth, shall be understood to refer to all such radially expandable tubular medical devices.

The inventive medical device delivery catheter in general and stent delivery catheter in particular, may be used for performing one or more intraluminal procedures on a patient as part of a therapeutic treatment. By "intraluminal," it is meant that the procedures occur at a target site within a body lumen. Typically, the procedure will occur within a portion of the patient vasculature such as, for example, the arterial system. More particularly, the inventive catheter will find use in the coronary arteries, the peripheral arteries and the cerebral arteries. The catheters of the present invention, however, are not limited to use in the vascular system and may also be advantageously employed in other body structures, including the prostate via the prostatic urethra, (e.g., to treat benign prostatic hypertrophy (BPH), or adenocarcinoma), the fallopian tube via its lumen (to treat strictures), brain parenchyma (to treat Parkinson's disease), and the like.

Figure 1:
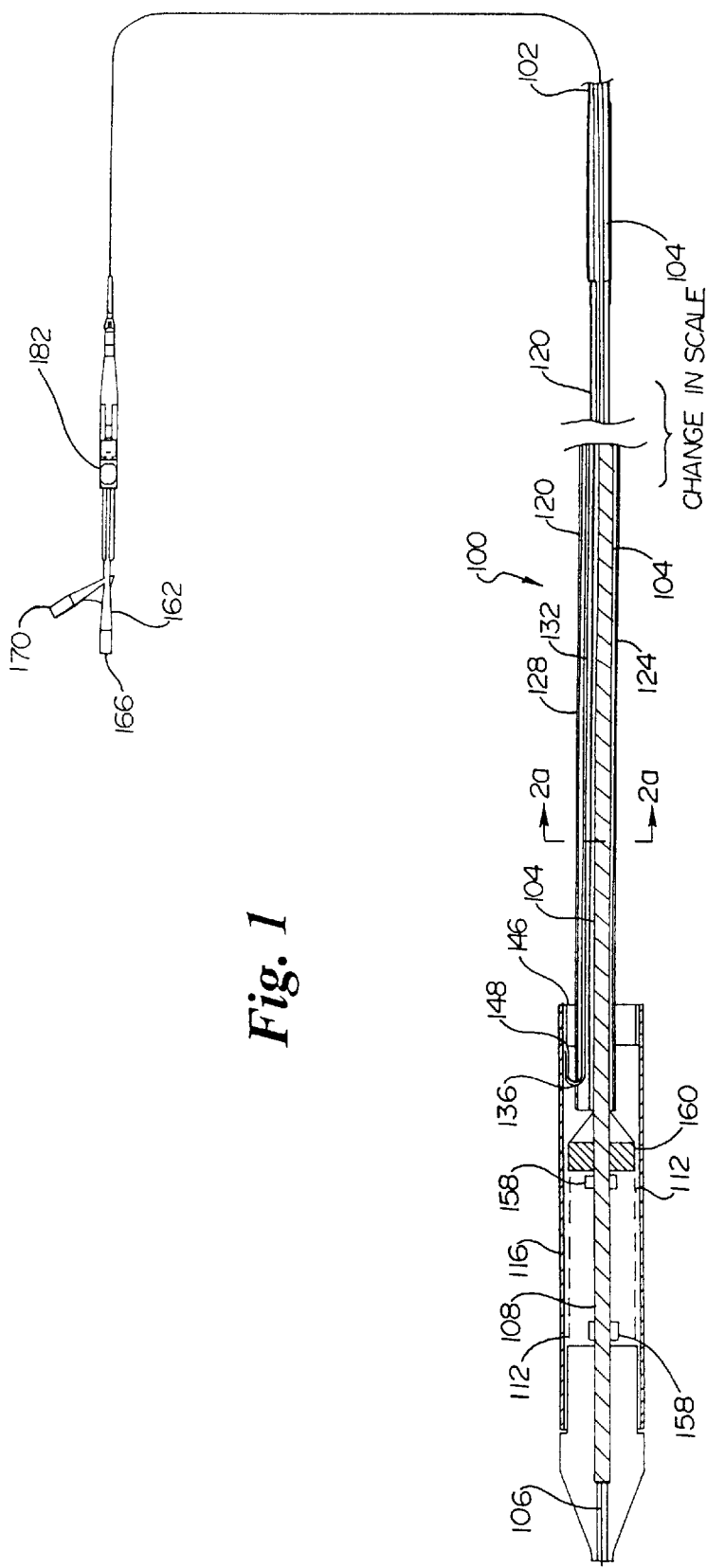
FIG. 1 shows a side elevational view of an inventive catheter with the distal end shown in cross-sectional view.

An over-the-wire embodiment of the inventive medical device delivery catheter is shown generally at 100 in FIG. 1.

Catheter 100 comprises an outer tube 102 which extends from the proximal end of the catheter. This outer tube 102 is characterized by a flexible tube which contains room for a pullwire and a guidewire lumen. Preferably, outer tube 102 is comprised of a polyimide and stainless steel ribbon composite material. Details of such an outer tube structure may be found, inter alia, in U.S. Pat. No. 5,772,669. Guidewire lumen 104 is disposed within outer tube 102 and carries guidewire 106 within.

The distal end of outer tube 102 is affixed to dual lumen tube 120 adhesively or through any other suitable means. The distal end of the outer tube is of larger outer diameter than the proximal end of dual lumen tube 120 allowing the proximal end of dual lumen tube 120 to fit inside the distal end of outer tube 102 for connection therebetween. The diameter of the proximal end of dual lumen tube 120 may also be larger than the diameter of outer tube 102 and the dual lumen tube fit over the outer tube.

Dual lumen tube 120, shown in transverse cross-section in FIG. 2a, includes an inner lumen 124 and a pullwire lumen 128. Guidewire lumen 104 is disposed within inner lumen 124. The guidewire may alternatively be carried directly in inner lumen 124 absent the guidewire lumen.

The distal end of guidewire lumen 104 extends distally from dual lumen tube 120 and has a medical device bearing region 108 about which a medical device, such as self-expanding stent 112, may be disposed. A retractable sheath 116 covers medical device bearing region 108.

Disposed within pullwire lumen 128 in dual lumen tube 120 is pullwire 132. Pullwire 132 exits pullwire lumen 128 at axial slit 136 in pullwire lumen 128. FIG. 2b shows a perspective view of dual lumen 120 highlighting slit 136. The length of slit 136 is sized to be approximately equal to the length of that portion of sheath 116 which begins at the proximal end of medical device bearing region 108 and terminates at the distal end of sheath 116. Slit 136 begins at the distal end of the pullwire lumen and extends proximally. At minimum, slit 136 must be long enough to allow for retraction of sheath 116 from over the medical device. Slit 136 may be as long as the retractable sheath or longer.

Pullwire 132 is welded, or otherwise attached, to pull collar 146 at point 148. Pull collar 146, in turn, is joined to retractable sheath 116 adhesively or otherwise. Desirably, pull collar 146 is slidably sealed to the exterior of dual lumen 120. The slidable seal may be accomplished in a variety of ways, as known in the art. Additional details on slidable seals may be found, inter alia, in U.S. Pat. No. 5,772,669 to Vrba et al. The sliding seal provides a leak-free seal between the pull collar and the dual lumen tube, thereby facilitating prepping of the catheter.

Pullwire 132 may, alternatively, be directly attached to retractable sheath 116 or otherwise in mechanical communication with sheath 116.

As shown in FIGS. 1 and 3, pullwire 132 extends slightly beyond its point of attachment 148 to pull collar 146 and loops back in the proximal direction. The catheter is shown with the sheath fully retracted in FIG. 3. The inventive catheters may also be constructed such that the pullwire extends entirely in the distal direction.

The inventive catheter may also be provided in an embodiment in which the dual lumen tube extends to the proximal end of the catheter. In such an embodiment, the presence of the outer tube is not necessary.

Figure 4:
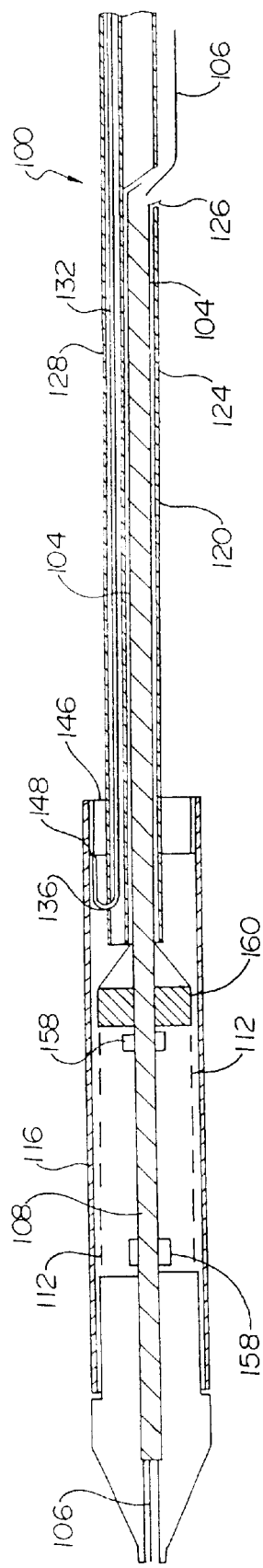
FIG. 4 shows a cross-sectional view of the distal end of an inventive catheter configured for use as a rapid exchange catheter.

A rapid exchange embodiment of the medical device delivery catheter is shown generally at 100 in FIG. 4. The catheter of FIG. 4 is similar to the catheter shown in FIG. 1, differing in that dual lumen tube 120 does not extend all the way to the proximal end of the catheter. Inner lumen 124 terminates in guidewire port 126 distal to the proximal end of catheter 100. Guidewire 106 enters inner lumen 124 through guidewire port 126.

Figure 5:
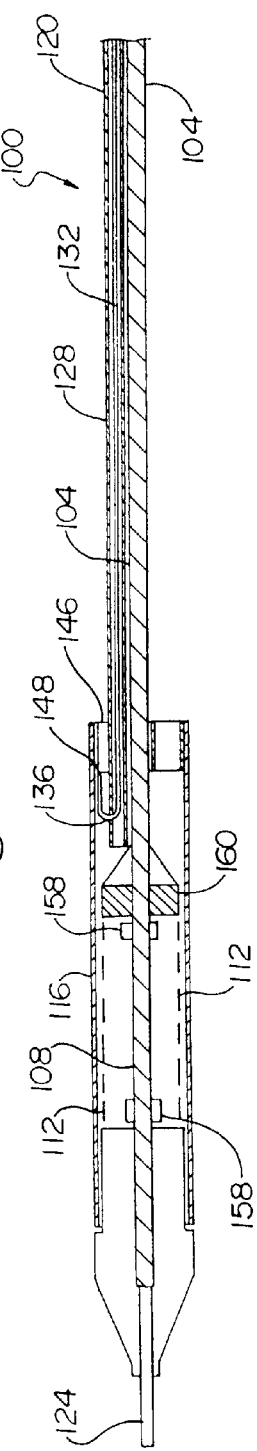
FIG. 5 shows a cross-sectional view of the distal end of an inventive catheter.

A fixed wire embodiment of the medical device delivery catheter is shown generally at 100 in FIG. 5. The catheter of FIG. 5 is similar to the catheter shown in FIG. 1, differing in that the dual lumen tube has been replaced by a single lumen 128 which serves as the pullwire lumen. The catheter further comprises an elongate shaft 104 which includes a medical device receiving region 108 about which a medical device such as stent 112 may be disposed. Tubular appendage 124 extends from shaft 104 and is similar to a guidewire lumen. Tubular appendage 124 may be of solid construction or hollow. The invention also contemplates providing a shaft or support separate from the pullwire lumen for receiving the medical device thereon. A wire 146 extends distally from the distal end of appendage 124.

The instant invention is also directed to catheters for balloon expandable medical devices such as balloon expandable stents. The catheter shown in FIG. 6a and in transverse cross-section in FIG. 6b, is similar to that shown in FIG. 1 and further comprises a medical balloon 150 disposed between stent 112 and medical device bearing region 108 of guidewire lumen 104. Medical balloon 150 is in fluid communication with an inflation lumen 123 which extends along shaft 104 and terminates in inflation lumen opening 125. The inflation lumen extends to the proximal end of the catheter. Inflation lumen 123 may be provided as a separate lumen. An example of such a configuration in which the inflation lumen is external to the guidewire lumen is shown in transverse cross-sectional view in FIG. 6c. The pullwire lumen may also be provided with a valve at the distal end to serve as an inflation lumen.

The rapid exchange and fixed-wire embodiments of the inventive catheter may also be similarly modified for use with a balloon expandable stent by providing a balloon and inflation lumen.

The inventive catheters may further comprise marker bands 158, desirably radiopaque, to facilitate positioning of the stent. The use of such marker bands is disclosed, inter alia, in U.S. Pat. No. 5,772,669. Other portions of the catheter may also have marker bands, as known in the art, to facilitate positioning of the catheter in the body.

The inventive catheters may further comprise one or more bumpers 160 adjacent to the stent or other medical device to be deployed. Bumper 160 may be of polyethylene and is affixed to guide wire lumen 104 by adhesive so as to prevent movement of stent 112 in a proximal direction when sheath 116 is retracted.

Figure 7:
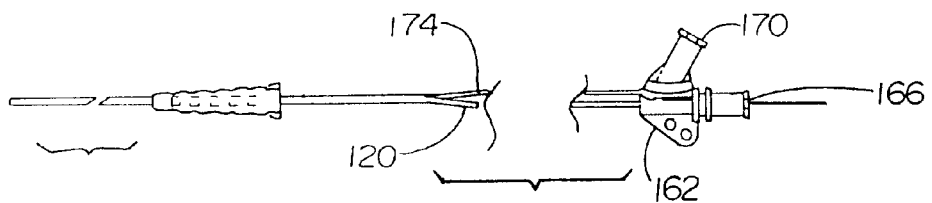
FIG. 7 shows a suitable manifold for use with the inventive catheters.

All of the inventive catheters further include a suitable manifold 162 at the proximal end of the device. A particularly suitable manifold for an over-the-wire version of the catheter is shown in greater detail in FIG. 7. Manifold 162 includes a guidewire port 166 through which a guidewire may be inserted into the guidewire lumen and a flush port 170 through which a suitable flushing fluid may be injected into the guidewire lumen. Extending from flush port 170 is a flush lumen 174 which is in fluid communication with guidewire lumen 104. Guidewire lumen 104 and flush lumen 174 may be welded together or otherwise suitably joined together. Additional details of the manifold construction may be found in copending, commonly assigned U.S. application Ser. No. 08/753,641.

Figure 8:
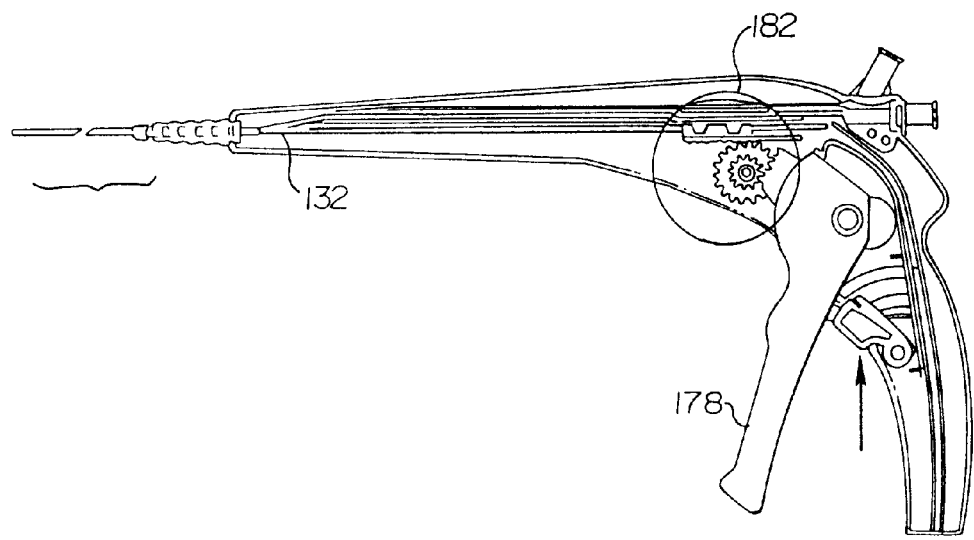
FIG. 8 shows a retraction mechanism suitable for use with the inventive catheter.
Figure 9:
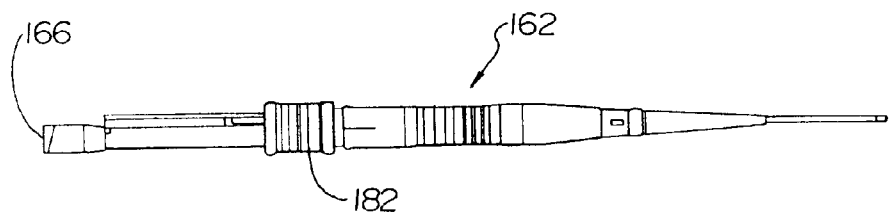
FIG. 9 shows a manifold suitable for use with the inventive catheter.

The rapid exchange and fixed wire embodiments of the inventive catheters may also employ a manifold similar to that shown in FIGS. 8 or 9 with suitable modifications or any other suitable manifold as known in the art.

Pullwire 132 is retracted using a suitable pullwire retraction mechanism arranged at the proximal ends of the pullwire lumen. One such suitable retraction mechanism is the ratchet mechanism such as that shown in FIG. 8. Trigger 178 is in mechanical communication with pullwire 132 via a ratchet mechanism, shown generally at 182. Pumping of trigger 178 results in proximal motion of pullwire 132 and retraction of sheath 116. Further details of the construction of the trigger mechanism may be found in copending, commonly assigned U.S. application Ser. No. 08/753,641. The pullwire may also be retracted using a retraction mechanism such as that shown in FIG. 1. Pullwire 132 is attached to slide 182 and may be moved proximally by moving slide 182 in a proximal direction. Such a manifold has been disclosed in U.S. Pat. No. 5,772,669 and elsewhere.

Pullwire 132 may also be retracted using any other suitable mechanisms as known in the art.

Another suitable manifold is shown in FIG. 9. Manifold 162 includes a guidewire lumen port 166. The pullwire is in mechanical communication with slide mechanism 182. An optional safety lock 184 may be used to prevent any unwanted movement of the slide mechanism.

Other suitable manifolds may also be used.

The inventive catheters may be further provided with an optional disposable cover disposed about the exterior of the catheter to provide leak-free prepping of the catheter.

The various portions of the catheter may be made of standard catheter materials as are known in the art. Dual lumen may be made of any suitable material such as, for example, high density polyethylene (HDPE). The guidewire lumen is desirably made of COBRAID® or similar materials such as disclosed in commonly assigned, copending U.S. application Ser. No. 09/033,724. Other suitable material known in the art may also be used in place of the COBRAID®. Any suitable guidewire may be used in conjunction with the invention. Suitable materials for the pull collar are disclosed in U.S. Pat. No. 5,772,669 as well as elsewhere.

Suitable balloon materials for use with those embodiments having a balloon are well known in the art and are described, inter alia, in U.S. Pat. No. 5,807,520 as well as in the references disclosed therein.

The various components of the inventive catheters may also be provided with suitable coatings as are known in the art. U.S. Pat. No. 5,443,907, and U.S. application Ser. Nos. 08/382,478, 09/306,939 and 09/316,502, for example, discloses suitable lubricious coatings for the interiors of various tubes commonly found in catheters.

The invention is also directed to methods of deploying a medical device such as a stent using an inventive catheter. A portion of the catheter is inserted into a bodily lumen and advanced to a desired bodily location. Where radiopaque marker bands are provided on the catheter, the location of the medical device bearing region of the catheter may be monitored via a suitable technique such as fluoroscopy. When the medical device is positioned at the desired bodily location, the pullwire is pulled in a proximal direction thereby retracting the sheath and exposing the medical device for deployment. In the case of a self-expanding stent, the stent will expand on retraction of the sheath. In the case of a balloon expandable stent, an inflation fluid is supplied to the balloon and the balloon expanded, thereby expanding the stent. The catheter may then be removed from the body with the stent left in place in the body.

In addition to the specific embodiments claimed below, the invention is also directed to other embodiments having any other possible combination of the dependent features claimed below.

The above disclosure is intended to be illustrative and not exhaustive. This description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claimed is:

1. A stent delivery catheter comprising:

a guidewire lumen for receiving a guidewire therein;

a stent disposed about the distal end of the guidewire lumen;

a retractable sheath disposed about the distal end of the guidewire lumen, the sheath covering the stent;

a pullwire lumen for receiving a pullwire therein, the pullwire lumen having a proximal end, a distal end and a region between the proximal and distal ends, the pullwire lumen extending to the proximal end of the catheter, the pullwire lumen having an axial slit of a predetermined length therein;

a pullwire disposed in the pullwire lumen, wherein the distal end of the pullwire extends distally, exits the pullwire lumen through the slit and loops back proximally so as to be in mechanical communication with the retractable sheath.

2. The stent delivery catheter of claim 1 further comprising an inner lumen, the guidewire lumen carried within the inner lumen.

3. The stent delivery catheter of claim 2 wherein the inner lumen and the pullwire lumen are of a single piece construction in the form of a dual lumen tube.

4. The stent delivery catheter of claim 3 further comprising a bumper extending from the distal end of the inner tube.

5. The stent delivery catheter of claim 1 wherein the slit begins and terminates proximal to the distal end of the pullwire lumen.

6. The stent delivery catheter of claim 1 wherein the pullwire is attached to the retractable sheath.

7. The stent delivery catheter of claim 1 further comprising a pull collar, the pull collar attached to the proximal end of the retractable sheath, the pullwire attached to the pull collar.

8. The stent delivery catheter of claim 1 in a form selected from the group consisting of rapid exchange and over-the-wire.

9. A stent delivery catheter comprising:
   a guidewire lumen for receiving a guidewire therein;
   a stent disposed about the distal end of the guidewire lumen;
   a retractable sheath disposed about the distal end of the guidewire lumen, the sheath covering the stent;
   a pullwire lumen for receiving a pullwire therein, the pullwire lumen having a proximal end, a distal end and a region between the proximal and distal ends, the pullwire lumen extending to the proximal end of the catheter, the pullwire lumen having an axial slit of a predetermined length therein wherein the slit begins at the distal end of the pullwire lumen;
   a pullwire disposed in the pullwire lumen, the distal end of the pullwire extending from the pullwire lumen through the slit and in mechanical communication with the retractable sheath.

10. The stent delivery catheter of claim 9, wherein the slit is at least as long as the stent.

11. The stent delivery catheter of claim 10 wherein the slit is longer than the stent.

12. The stent delivery catheter of claim 11 wherein the length of the slit is approximately equal to the length of that portion of the sheath which begins at the proximal end of the stent and terminates at the distal end of the sheath.

13. A stent delivery catheter comprising:
   a guidewire lumen for receiving a guidewire therein;
   a stent disposed about the distal end of the guidewire lumen;
   a retractable sheath disposed about the distal end of the guidewire lumen, the sheath covering the stent;
   a pullwire lumen for receiving a pullwire therein, the pullwire lumen having a proximal end, a distal end and a region between the proximal and distal ends, the pullwire lumen extending to the proximal end of the catheter, the pullwire lumen having an axial slit of a predetermined length therein;
   a pullwire disposed in the pullwire lumen, the distal end of the pullwire extending from the pullwire lumen through the slit and in mechanical communication with the retractable sheath;
   an inner tube, the guidewire lumen disposed in the inner tube and wherein the inner tube and the pullwire lumen are of a single piece construction in the form of a dual lumen tube, and the slit begins at the distal end of the pullwire lumen, the length of the slit approximately equal to the length of that portion of the sheath which begins at the proximal end of the stent and terminates at the distal end of the sheath.

14. A medical device delivery catheter comprising:
   an inner tube, a portion of the distal end of the inner tube having a medical device bearing region,
   a retractable sheath disposed about the medical device bearing region of the inner tube,
   a pullwire lumen for carrying a pullwire therein, the pullwire lumen extending to the proximal end of the catheter, a portion of the pullwire lumen having an axial slit therein,
   a pullwire disposed in the pullwire lumen, the distal end of the pullwire extends distally and exits the pullwire lumen through the slit and loops back proximally so as to be in mechanical communication with the retractable sheath,
   a pullwire disposed in the pullwire lumen, wherein the distal end of the pullwire extends distally, exits the pullwire lumen through the slit and loops back proximally so as to be in mechanical communication with the retractable sheath.

15. The medical device delivery catheter of claim 14 further comprising a medical device disposed about the medical device bearing region of the inner tube.

16. The medical device delivery catheter of claim 15, wherein the medical device is selected from the group consisting of stents, stent-grafts, grafts and vena cava filters.

17. The medical device delivery catheter of claim 14 wherein the inner tube terminates distal to the distal end of the pullwire lumen.

18. The medical device delivery catheter of claim 14, in a form selected from the group consisting of rapid exchange, over-the-wire and fixed wire.

19. A medical device delivery catheter comprising:
   an inner tube, a portion of the distal end of the inner tube having a medical device bearing region,
   a retractable sheath disposed about the medical device bearing region of the inner tube,
   a pullwire lumen for carrying a pullwire therein, the pullwire lumen extending to the proximal end of the catheter, a portion of the pullwire lumen having an axial slit therein,
   a pullwire disposed in the pullwire lumen, the distal end of the pullwire loops back in a proximal direction after exiting the pullwire lumen through the slit, the pullwire in mechanical communication with the retractable sheath.

20. A medical device delivery catheter comprising:
   an inner tube, a portion of the distal end of the inner tube having a medical device bearing region,
   a retractable sheath disposed about the medical device bearing region of the inner tube,
   a pullwire lumen for carrying a pullwire therein, the pullwire lumen extending to the proximal end of the catheter, a portion of the pullwire lumen having an axial slit therein, wherein the slit is longer than the medical device,
   a pullwire disposed in the pullwire lumen, the distal end of the pullwire exiting the pullwire lumen through the slit, the pullwire in mechanical communication with the retractable sheath,
   a medical device disposed about the medical device bearing region of the inner tube.

21. A medical device delivery catheter comprising:
   an inner tube, a portion of the distal end of the inner tube having a medical device bearing region,
   a retractable sheath disposed about the medical device bearing region of the inner tube,
   a pullwire lumen for carrying a pullwire therein, the pullwire lumen extending to the proximal end of the catheter, a portion of the pullwire lumen having an axial slit therein, wherein the length of the slit is approximately equal to the length of that portion of the sheath which begins at the proximal end of the stent and terminates at the distal end of the sheath,
   a pullwire disposed in the pullwire lumen, the distal end of the pullwire exiting the pullwire lumen through the slit, the pullwire in mechanical communication with the retractable sheath, a medical device disposed about the medical device bearing region of the inner tube.

22. The medical device delivery catheter of claim 21, further comprising a manifold and a pullwire retraction mechanism arranged at the proximal end of the pullwire lumen.

23. The medical device delivery catheter of claim 21 wherein the inner tube extends to the manifold.

24. The medical device delivery catheter of claim 21 wherein the pullwire lumen and inner tube are of a single piece construction in the form of a dual lumen tube, the catheter further comprising a manifold and a pullwire retraction mechanism arranged at the proximal end of the catheter in mechanical communication with the pullwire and an outer tube extending distally from the manifold, the distal end of the outer tube affixed to a proximal end of the dual lumen tube.

* * * * *